(12) United States Patent
Ghosh Roy

(10) Patent No.: US 12,414,703 B2
(45) Date of Patent: Sep. 16, 2025

(54) MEDICAL DEVICE SYSTEM FOR REMOTE MONITORING AND INSPECTION

(71) Applicant: MOZARC MEDICAL US LLC, Minneapolis, MN (US)

(72) Inventor: Arindam Ghosh Roy, Bangalore (IN)

(73) Assignee: Mozarc Medical US LLC, Minneapolis, MN (US)

(\*) Notice: Subject to any disclaimer, the term of this patent is extended or adjusted under 35 U.S.C. 154(b) by 791 days.

(21) Appl. No.: 17/392,042

(22) Filed: Aug. 2, 2021

(65) Prior Publication Data

US 2023/0029639 A1  Feb. 2, 2023

(51) Int. Cl.
| | |
|---|---|
| *A61B 5/026* | (2006.01) |
| *A61B 5/00* | (2006.01) |
| *A61B 5/01* | (2006.01) |
| *A61B 5/145* | (2006.01) |

(52) U.S. Cl.
CPC .............. *A61B 5/026* (2013.01); *A61B 5/01* (2013.01); *A61B 5/14542* (2013.01); *A61B 5/6813* (2013.01); *A61B 5/7275* (2013.01); *A61B 5/7405* (2013.01); *A61B 5/742* (2013.01); *A61B 5/7455* (2013.01); *A61B 2562/0271* (2013.01); *A61B 2562/08* (2013.01)

(58) Field of Classification Search
CPC ......... A61B 5/026; A61B 5/01; A61B 5/6813; A61B 5/7275; A61B 5/7405
See application file for complete search history.

(56) References Cited

U.S. PATENT DOCUMENTS

| | | | |
|---|---|---|---|
| 9,579,060 B1* | 2/2017 | Lisy | A61B 5/4803 |
| 2004/0249293 A1* | 12/2004 | Sandler | A61B 7/00 600/528 |
| 2013/0245391 A1* | 9/2013 | Hyde | A61B 5/6885 600/490 |
| 2019/0117156 A1* | 4/2019 | Howard | A61B 5/1126 |
| 2019/0192015 A1* | 6/2019 | Campo | A61B 7/026 |
| 2020/0319770 A1* | 10/2020 | Varga | G06F 3/04815 |
| 2020/0330011 A1* | 10/2020 | Honore | A61B 5/1455 |
| 2020/0337638 A1* | 10/2020 | Peesapati | A61B 5/14542 |
| 2021/0259560 A1* | 8/2021 | Venkatraman | A61B 5/024 |

\* cited by examiner

*Primary Examiner* — Eric F Winakur

(57) ABSTRACT

A medical system includes a medical device with processing circuitry configured to receive sensor data and send the sensor data to a diagnostic system. The sensor data includes sound data associated with blood flow and vibration data associated with blood flow. The diagnostic system includes a computing system configured to receive the sensor data and output devices. The output devices include a speaker configured to output a sound based on the sound data and a haptic device configured to provide a haptic feedback based on the vibration data.

17 Claims, 8 Drawing Sheets

MEDICAL DEVICE SYSTEM FOR REMOTE MONITORING AND INSPECTION

TECHNICAL FIELD

This disclosure relates to medical device systems for monitoring a patient's health.

BACKGROUND

Patients with renal disease may receive hemodialysis treatment, which may involve using a medical machine, (e.g., a hemodialysis system including one or more of a dialyzer, artificial kidney, etc.) to remove blood from the body, filter waste and extra fluid from the blood, balance electrolytes, and return the blood to the body. To perform hemodialysis, an access may be created to allow blood to flow from the body to the medical machine and back to the body. Access types for hemodialysis may include an arteriovenous (AV) fistula, which may be surgically created with an anastomosis of an artery and a vein. AV fistula dysfunction can happen over time, and complications related to AV fistula dysfunction may lead to hospitalization for hemodialysis patients. Preventing the development of complications can reduce morbidity, improve quality of life, and reduce the cost of health care in the dialysis population.

SUMMARY

To detect arteriovenous (AV) fistula dysfunction, patients receiving hemodialysis treatment (e.g., at home, at a clinic, etc.) may visit a healthcare professional, such as a physician, for inspection. During the visit, the healthcare professional may physically examine the patient to detect evidence of stenosis or thrombosis. The examination may include visual inspection of an AV access site, palpation to feel for a thrill at and/or around the AV access site, auscultation with a stethoscope to identify any changes in a bruit, and/or the like. While visits with the healthcare professional may be relatively short, visits can still constitute a burden on the physician's clinic and on the healthcare system overall. In-person visits with a healthcare professional may be difficult or otherwise inconvenient for the patient as well.

Aspects of this disclosure are directed to techniques for remotely monitoring a patient to facilitate inspection of the patient. In some examples, a medical system comprises: a medical device, configured to be positioned on a limb of a patient, comprising sensors, wherein the sensors comprise: sound sensors; and vibration sensors; processing circuitry configured to: receive sensor data comprising: sound data, associated with blood flow, collected by the sound sensors; and vibration data, associated with blood flow, collected by the vibration sensors; and send the sensor data to a computing system.

In some examples, a diagnostic system comprises: a computing system configured to: receive sensor data from a processing circuitry, the sensor data comprising: sound data associated with blood flow; vibration data associated with blood flow; output devices comprising: a speaker configured to output a sound based on the sound data; and a haptic device configured to provide a haptic feedback based on the vibration data.

In some examples, a method comprises: measuring, by sensors of a medical device, one or more physiological parameters of a patient, wherein the medical device is configured to be positioned on a limb of the patient, and wherein the sensors comprise sound sensors and vibration sensors; outputting, by the sensors, sensor data to processing circuitry, wherein the sensor data comprises sound data associated with blood flood and vibration data associated with blood flow; and sending, by the processing circuitry, the sensor data to a computing system.

The details of one or more examples are set forth in the accompanying drawings and the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
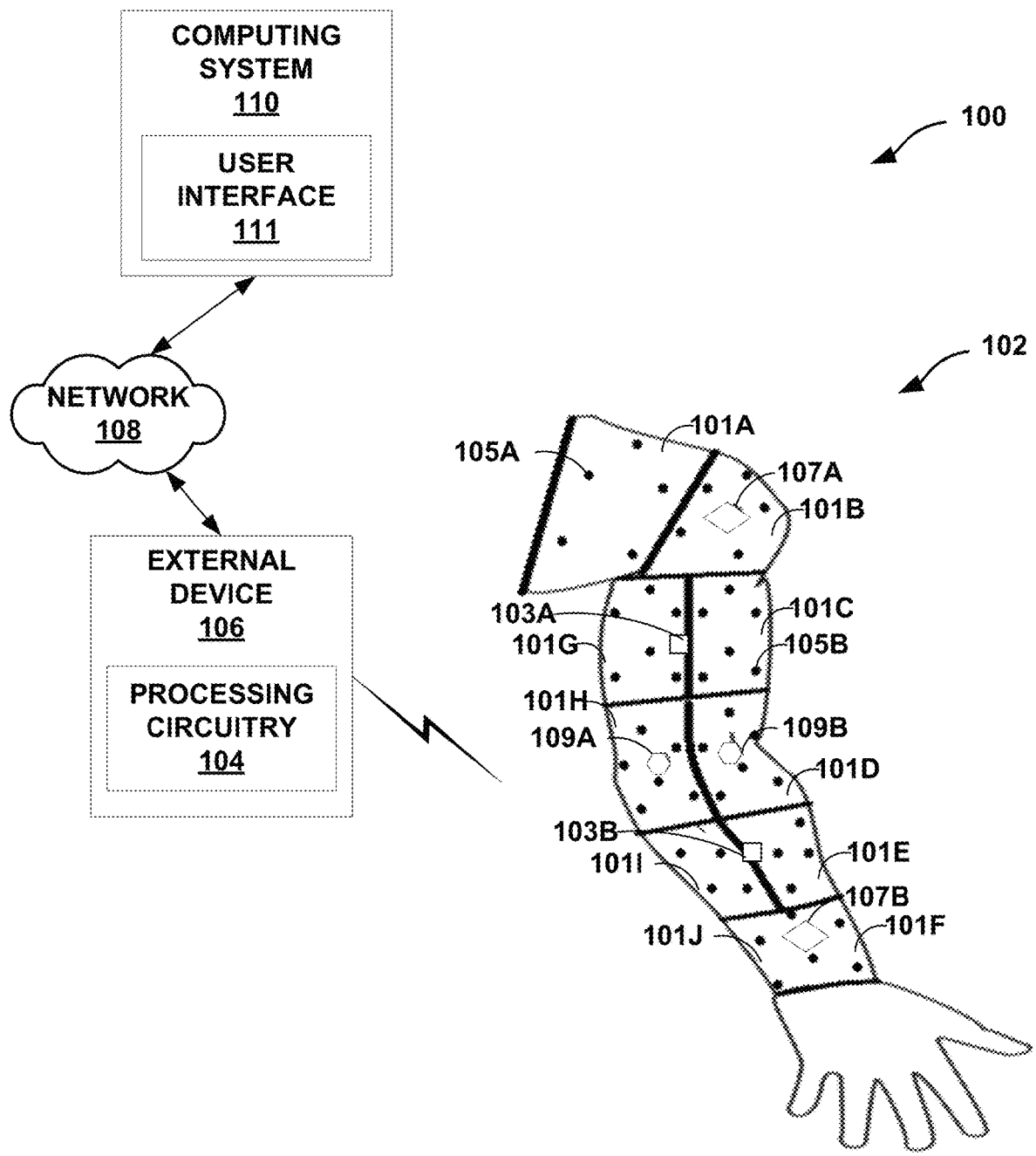
FIG. 1 is a conceptual diagram of an example monitoring system.

This disclosure describes a medical system configured to enable remote monitoring of a patient and to facilitate inspection of the patient. In some examples, the medical system may include a medical device in contact with the patient, an external device in close-range communication with the medical device, and a computing system. The medical device may include circuitry (e.g., processing circuitry, sensing circuitry, etc.) configured to generate sensor data indicative of a medical condition, such as arteriovenous (AV) fistula dysfunction. The sensor data may include, but is not limited to, sound data associated with blood flow and vibration data associated with blood flow.

As used herein, sound may be distinguished from vibration in that the term 'sound' generally connotes an alteration in pressure, stress, particle displacement, and particle velocity, which is propagated, in an elastic material, or the superposition of such propagated alterations (such that the sound can be heard by a human ear), whereas the term vibration generally connotes an implication that all the particles in a finite region are moving in phase (such that the vibration can be felt by, e.g., a human finger). Parameters for sound may include frequency (Hz) and decibels (dB). Parameters for vibration may include Hz and acceleration (e.g., in terms of gravity (g)). Due to the varying physical properties for sound and vibration devices may need to be configured one way to measure sound and in another way to measure vibration. Accordingly, sound data may be captured by a microphone or similar audio recording equipment known in the art, and vibration data may be captured by an accelerometer or other vibration sensor known in the art.

The external device may be configured to receive the sensor data collected by the medical device and send the sensor data to a computing system. The computing system may be configured to output (via one or more output devices) the sensor data in a form (e.g., a sound, haptic feedback, a virtual model, etc.) that a user, such as a physician, may use to monitor and diagnose the patient.

The medical device may be a wearable device, such as a sleeve configured to be positioned on a limb of a patient. For example, the sleeve may wrap around the perimeter of an arm of the patient and be secured using an attachment mechanism, such as a hook-and-loop closure, to maintain the position of the sleeve. The sleeve may include a variety of sensors to collect sensor data. For example, the sleeve may include one or more sound, or acoustic, sensors configured to collect sound data, one or more vibration sensors configured to collect vibration data, one or more temperature sensors configured to collect temperature data, one or more pulse sensors configured to collect pulse data, and/or other sensors configured to collect data associated with one or more physiological parameters of a patient. The sensors may be arranged such that the sensors may collect sensor data along the perimeter and length of the limb. In this way, the medical device may collect sensor data from a variety of locations on the limb, which may assist in detection of a medical condition. The sleeve may be positioned such that one or more sensors are aligned with the AV access site.

One or more components of the medical system may include processing circuitry configured to send the sensor data to a computing system. For example, an external device (e.g., a smartphone, a tablet computer, etc.), a medical machine (e.g., a hemodialysis system including one or more of a dialyzer, artificial kidney, etc.), the medical device, and/or the like may include the processing circuitry. As such, the processing circuitry may be implemented in various ways to perform one or more techniques of this disclosure. In some examples, the processing circuitry may be configured to wirelessly communicate with the computing system via a network.

The computing system may be configured to receive the sensor data from the processing circuitry and to output, via a user interface including one or more output devices, the sensor data in a form that a user (e.g., a physician) may use to monitor the patient. For example, the user interface of the computing system may include a computing device (e.g., a smartphone, laptop computer, tablet computer, computer workstations, etc.), a speaker configured to output a sound based on the sound data, a haptic device configured to provide haptic feedback based on the vibration data, a display configured to output visual information (e.g., indicators, diagrams, metrics, graphical user interfaces (GUIs), etc.) based on the sensor data (e.g., sound data, vibration data, temperature data, etc.), etc. The user interface may further include a wearable visualization device, such as an extended reality (ER) headset (e.g., an augmented reality (AR) headset, a virtual reality (VR) headset, mixed reality (MR) headset, etc.) configured to output visual information (e.g., virtual objects, indicators, diagrams, metrics, GUIs, etc.) to a user (e.g., a physician) in real-time or near real-time.

The visualization device may allow a user to manipulate a GUI when wearing the visualization device to select a virtual analog (e.g., a virtual object representing and/or corresponding to a physical object) of a particular sensor of a medical device to trigger output, via one or more output devices, of a portion of the sensor data collected by the particular sensor. In some examples, the visualization device may be configured to present virtual objects such that a user sees images that include both real, physical objects and virtual objects. Virtual objects may include text, 2-dimensional surfaces, 3-dimensional models, or other user-perceptible elements that are not actually present in the physical, real-world environment in which the virtual objects are presented as coexisting. For example, the visualization device may present the medical device worn by the patient as a virtual object to the user of the visualization device. In some examples, virtual objects may include graphics, images, animations or videos, e.g., presented as 3D virtual objects or 2D virtual objects. Virtual objects may or may not be analogs of real-world objects.

In some examples, the visualization device may be configured to present a mixed reality using see-through (e.g., transparent) holographic lenses, which may be referred to as waveguides. The waveguides may permit the user to view real-world objects, i.e., actual objects in a real-world environment, such as the physical surroundings of the user, through the holographic lenses and also concurrently view virtual objects. In some examples, some holographic lenses may, at times, completely prevent the user from viewing real-world objects and instead may allow the user to view entirely virtual environments.

Accordingly, the user interface of the computing system may provide a variety of feedback via one or more output devices (e.g., speakers, haptic devices, visualization devices, etc.) and based on the sensor data to enable remote monitoring of a patient. For example, a user of the computing system may wear an AR headset with built-in speakers configured to emit sound (e.g., a rumbling sound resembling a bruit) and holographic lenses configured to present virtual objects (e.g., virtual analogs of the medical device, the haptic device, etc.). The user may also wear a haptic glove including one or more haptic actuators configured to provide a haptic feedback (e.g., a rumbling vibration resembling a thrill) based on the vibration data.

In some examples, the visualization device may include a variety of sensors to collect sensor data for producing virtual analogs of the geometry of the user of the visualization device and, optionally, the geometry of the physical environment in which the user is located (e.g., an examination room). For example, the visualization device may include one or more optical cameras (or other optical sensors) and one or more depth camera(s) (or other depth sensors), mounted to, on, or within a frame of the visualization device. In some examples, the optical sensors are operable to collect two-dimensional (2D) optical image data (either monochrome or color), and the depth sensors are operable to provide 3D image data, such as by employing time of flight, stereo or other known or future-developed techniques for determining depth and thereby generating image data in three dimensions. Other sensors can include motion sensors (e.g., Inertial Mass Unit (IMU) sensors, accelerometers, etc.) to assist with tracking movement. Thus, by using these sensors, the visualization device may simulate movements, dimensions, shapes, angles, surface contours, orientations, and other physical properties of real-world objects (e.g., the hands of the user) in the virtual reality.

As described above, the haptic device may be configured to provide a haptic feedback, such as a rumbling vibration resembling a thrill, based on the vibration data. A user of the haptic device may select at least a portion of the vibration data, such as the vibration data from a particular vibration sensor of the medical device, to be provided as haptic feedback to the user. For example, the user may select, in the virtual reality presented by the visualization device, the portion of the vibration data associated with a particular vibration sensor of the medical device by moving the hand wearing the haptic device in the real-world such that the virtual analog of the haptic device is contacting (e.g., touching, proximate to, etc.) with the virtual analog of the particular vibration sensor. Responsive to (and, optionally, only for the duration of) such contact between the virtual analogs, the haptic actuators of the haptic device may provide haptic feedback based on the portion of vibration data associated with the particular vibration sensor. Similarly, the user may cause the user interface of the computing system to output sound based on the portion of sound data associated with a particular sound sensor (e.g., by selecting the sound sensor in the virtual reality presented by the visualization device).

In this way, the medical system may enable a user (e.g., a physician, a telehealth provider, etc.) to remotely perform palpation (e.g., by using a haptic device, such as a haptic glove) to feel a thrill at and around an AV access site of a patient and/or auscultation (e.g., by using speakers that may or may not be built into a head-wearable device, such as an AR headset) to hear a bruit (e.g., a rumbling sound). Moreover, the medical system may include a visualization device with which the user can view and interact with virtual objects to increase the similarity between the experience of performing a remote examination and an in-person examination. For instance, to cause the computing system to output feedback (e.g., audio, tactile, etc.) associated with a particular sensor, the user may select the sensor by contacting (e.g., touching, proximate to, etc.) a virtual analog of the particular sensor with a virtual analog of a part of a user's body (e.g., the user's hand). Thus, the techniques described herein may increase access to medical examinations by enabling the performance of remote examinations that are, similar, if not substantially similar, to in-person examinations, in this way potentially improving patient outcomes (e.g., by resulting in earlier identification of AV fistula dysfunction).

FIG. 1 illustrates a medical system 100 ("system 100") in conjunction with a patient. In the example of FIG. 1, system 100 includes at least one medical device 102, processing circuitry 104, an external device 106, and a computing system 110. As shown in FIG. 1, medical device 102 may be a wearable device, such as a sleeve or any other external medical devices configured to be positioned on a patient to obtain physiological data of patient. In examples where medical device 102 is a sleeve, medical device 102 may be configured with any suitable dimensions (e.g., shape, size, length, width, thickness, and the like) to facilitate positioning medical device 102 on a limb (e.g., an arm of a patient) or other body part of interest. For example, the size of medical device 102 may vary to accommodate various patient sizes (e.g., a small child, an adult woman, an adult male, and the like). A plurality of medical devices 102 having different sizes may be made available to a clinician and the clinician may select an appropriate medical device 102 from the plurality of medical devices 102 based on the patient size.

Medical device 102 may include circuitry configured to generate sensor data based on signals from sensors of medical device 102. Medical device 102 may include subregions 101A-101J (collectively, "subregions 101"), and the sensors may be located in subregions 101. In general, each type of sensor, described in greater detail below, of medical device 102 may be located in one or more of subregions 101. For example, each type of sensor may be located in each of subregions 101. Persons of skill in the art should understand that the depiction of subregions 101 shown in FIG. 1 is for purposes of illustration and that properties of subregions 101, such as the number, size, shape, location, etc., of subregions 101 may vary. Accordingly, the example of medical device 102 shown in FIG. 1 is not intended to be limiting, and variations of the properties of subregions 101 are contemplated by this disclosure.

In some examples, medical device 102 may include one or more sound sensors such as sound sensors 103A-103B (collectively, sound sensors 103). Sound sensors 103 configured to detect sound in the range of 20 hertz (Hz) to 10,000 Hz (which may facilitate detection of a bruit through auscultation). Examples of sound sensors 103 may include contact microphones, electric condenser microphones, piezoresistive sound sensor, etc. In some examples, sound sensors 103 may record the time domain sound waves with a sampling rate of 22000 Hz in WAV lossless format, although other sampling rates, file formats, etc., are possible.

Medical device 102 may also include one or more vibration sensors, such as vibration sensors 105A-105B (collectively, "vibration sensors 105"). Vibration sensors 105 may be configured to measure force, acceleration, etc., and output sensor data (e.g., electric signals) corresponding to the measurements to circuitry. In other words, the circuitry may collect the sensor data from vibration sensors 105. Examples of vibration sensors 105 may include accelerometers, piezoelectric sensors, etc. In some examples, medical device 102 may include one or more temperature sensors, such as temperature sensors 107A-107B (collectively, "temperature sensors 107"). Temperatures sensors 107 may be configured to measure temperature and output sensor data corresponding to the measurements to circuitry. Examples of temperatures sensors may include thermocouples, resistance temperature detectors, etc. Additionally or alternatively, medical device 102 may include one or more pulse sensors, such as pulse sensors 109A-109B (collectively, "pulse sensors 109"). Pulse sensors 109 may be configured to measure the pulse (or another physiological parameter correlated with pulse) and output sensor data corresponding to the measurements to circuitry. Examples of pulse sensors may include oximeters.

Thus, a person of skill in the art should understand that medical device 102 may include any type of sensor configured to measure one or more physiological parameters of a patient and output sensor data corresponding to the measurements to the circuitry, in this way collecting sensor data. Further, it should be apparent that the number of sensors (e.g., sound sensors 103, vibration sensors 105, temperature sensors 107, pulse sensors 109, etc.) shown in FIG. 1 is for purposes of illustration only. Accordingly, medical device 102 may include fewer or more of each type of sensor.

In any case, the sensors may be arranged such that the sensors may collect sensor data along various positions (e.g., various axial positions of a limb, various longitudinal positions of a limb, etc.). In examples, each sensor may have a unique position with respect to medical device 102 (and more specifically with respect to subregions 101) as well as unique identification information (e.g., each sensor may be tagged) that is transmitted with the sensor data to allow for the derivation of location data. In other words, processing circuitry may be configured to send the sensor data collected by each sensor with the unique identification information of the sensor. For example, medical device 102 may be configured such that sound sensor 103A is located in a predetermined area of subregion 101G. Computing system 110 may receive sensor data from medical device 102 and determine that at least a portion of the sensor data was collected by sound sensor 103A based on the unique identification information. Computing system 110 may in turn determine a location on a limb of a patient proximal to (e.g., at and/or around) the predetermined area of subregion 101G when medical device 102 is positioned on (e.g., worn) by the limb of the patient. Such location data may be helpful to a clinician by accurately indicating to the clinician the part of the patient's limb producing the bruit or thrill, which may inform the clinician's diagnosis of stenosis, thrombosis, etc.

In this way, medical device 102 may collect sensor data from a variety of locations on the limb, which may assist detection of a medical condition, as the data collected by the sensors may vary based on location. For example, if there is a stenosis upstream of pulse sensor 109, pulse sensor 109 may detect a weaker than average pulse; if there is a stenosis downstream, pulse sensor 109 may detect a stronger than average pulse. In some examples, medical device 102 may be positioned such that one or more sensors are aligned with the AV access site.

As shown in FIG. 1, external device 106, such as a computing device (e.g., a smartphone, a tablet computer, a laptop, etc.), may include processing circuitry 104. In some examples, external device 106 may provide a user interface and allow a user to interact with medical device 102. While primarily discussed in relation to external device 106, it should be understood that processing circuitry 104 may be included in other components of system 100, such as medical device 102 or a medical machine (e.g., a hemodialysis system, etc.). In any case, processing circuitry 104 may operate in a substantially similar manner to perform one or more techniques of this disclosure irrespective of which component or components of system 100 includes processing circuitry 104.

Processing circuitry 104 may be configured to receive sensor data from medical device 102. For example, external device 106 may be configured to communicate with medical device 102 via wired or wireless communication. In some examples, external device 106 may communicate via near-field communication (NFC) technologies (e.g., inductive coupling, NFC or other communication technologies operable at ranges less than 10-20 cm) and/or far-field communication technologies (e.g., Radio Frequency (RF) telemetry according to the 802.11, Bluetooth® specification sets, or other communication technologies operable at ranges greater than NFC technologies. Additionally or alternatively, external device 102 may communicate via a cellular radio, a 3G radio, a 4G radio, a 5G radio, or a WiFi® radio (or any other wireless local area network (WLAN) radio). The sensor data external device 106 receives from medical device 102 may include historical data stored to memory of medical device 102, and/or real-time data collected by medical device 102. Example types of sensor data may include sound data, vibration data, and other data about physiological parameters.

In some examples, processing circuitry 104 may be configured to evaluate the sensor data and, based on the evaluation of the sensor data, send at least a portion of the sensor data to computing system 110. For example, processing circuitry 104 may be configured to process the sensor data to determine whether a risk of the occurrence of at least one of stenosis or thrombosis exceeds a respective threshold risk for each of those conditions. That is, processing circuitry 104 may be configured to process the sensor data to determine whether a likelihood of the occurrence of the at least one of the stenosis or the thrombosis exceeds a threshold risk of the occurrence of the at least one of the stenosis or the thrombosis. As an example, processing circuitry 104 may evaluate a risk of occurrence of stenosis or thrombosis based on the difference between the current levels of various physiological parameters (e.g., temperature, pulse, etc.) and baseline levels (e.g., the average levels for a particular patient during a prior time period) of those various physiological parameters. If the difference between the current levels of various physiological parameters and baseline levels satisfies a predetermined threshold (e.g., the current temperature is 20% lesser than the baseline temperature), processing circuitry 104 may determine that the risk of occurrence of stenosis or thrombosis exceeds the respective threshold risk for each of those conditions. Responsive to such a determination, processing circuitry 104 may store the portion of sensor data collected during the session when the risk of occurrence of stenosis or thrombosis exceeded the threshold risk and transmit that portion of sensor data to computing system 110 in accordance with techniques of this disclosure. Additionally, processing circuitry 104 may send an indication to computing system 110 that the threshold risk of the occurrence of the at least one of the stenosis or the thrombosis is satisfied.

In some examples, the algorithm executed by processing circuitry 104 may involve evaluating the morphology of sensor data in the detection and discrimination of AV fistula dysfunction. In some examples, processing circuitry 104 may use a template comparison algorithm to compare the sensor data to template sensor data corresponding to a predetermined template of a medical condition. Based on the template comparisons, processing circuitry 104 may classify the sensor data as indicative of AV fistula dysfunction and send the sensor data to computing system 110. For example, processing circuitry 104 may compare a portion of audio data collected during a session to template audio data indicative of one or more of stenosis or thrombosis. In such an example, processing circuitry 104 may use audio processing techniques known in the art to compare the waveform of the portion of audio data collected during the session to the waveform of the template audio data. If the differences satisfies a predetermined threshold (e.g., the similarity between the portion of audio data collected during the session to the template audio data is at least 70% identical or similar), processing circuitry 104 may determine that the risk of occurrence of stenosis or thrombosis exceeds the respective threshold risk for each of those conditions and store the portion of sensor data in memory for subsequent transmittal to a computing system 10. A network 108 may enable communication between external device 106 and computing system 110.

Computing system 110 may include computing devices configured to allow a user, such as a physician, to interact with the sensor data collected from medical device 102, via network 108. In some examples, computing system 110 may include one or more handheld computing devices, computer workstations, servers or other networked computing devices. In some examples, computing system 110 may include one or more devices, including processing circuitry and storage devices, that implement a monitoring system. In some examples, computing system 110 may periodically transmit and/or receive various data items, via network 108, to and/or from external device 106. In some examples, external device 106 may transmit and/or receive various data items, via network 108, to and/or from external device 106 in real-time (i.e., such that input data are processed within milliseconds so that the input data are available virtually immediately as feedback) or near real-time. Thus, computing system 110 and external device 106 may be used to enable a real-time, remote physical examination of a patient.

Network 108 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 108 may include one or more networks administered by service providers, and may thus form part of a large-scale public network infrastructure, such as the Internet. Network 108 may provide computing devices, such as computing system 110 and medical device 102, access to the Internet, and may provide a communication framework that allows the computing devices to communicate with one another. In some examples, network 108 may be a private network that provides a communication framework that allows computing system 110, medical device 102, and/or external device 106 to communicate with one another but isolates one or more of computing system 110, medical device 102, or external device 106 from devices external to network 108 for security purposes. In some examples, the communications between computing system 110, medical device 102, and external device 106 are encrypted.

Computing system may be configured to receive the sensor data from processing circuitry 104 and to output the sensor data via a user interface 111 including one or more output devices. In some examples, the output devices are configured to provide output to a user using video, tactile, and/or audio stimuli. An example output device is a visualization device. In some examples, the visualization device is wearable by a user. In some examples, the visualization device is held by a user, or rests on a surface in a place accessible to the user. The visualization device may present a GUI that is visually perceptible to the user using the visualization device. For instance, in one example, a screen of the visualization device may display real-world images and the GUI on a screen. The GUI may be configured to include, for example, temperature data (e.g., a measured body temperature), pulse data (e.g., a measured pulse rate), and other sensor data indicative of the physiological parameters of the patient in a manner comprehensible to a user (e.g., as indicators, diagrams, metrics, etc.).

In some examples, the visualization device may project virtual, holographic images onto see-through holographic lenses and also permit a user to see real-world objects of a real-world environment through the lenses. In other words, the visualization device may include one or more see-through holographic lenses and one or more display devices that present imagery to the user via the holographic lenses to present the GUI to the user.

In some examples, the visualization device is configured such that the user can manipulate the GUI (which is visually perceptible to the user when the user is wearing or otherwise using the visualization device) to request and view information, including, but not limited to, at least a portion of the sensor data being collected by the medical device for the particular patient. For example, the user may view a 3D virtual model of the anatomy of interest (e.g., a 3D virtual model of an arm of the patient wearing the medical device) and the location of the sensors of the medical device relative to the 3D virtual model. In some such examples, the visualization device is configured such that the user can manipulate the GUI to, for example, more conveniently select a particular sensor in accordance with techniques described herein.

The output devices may include a speaker or other sensory device configured to output sound based on the sound data. In some examples, the visualization device may include such a sensory device, which may be positioned adjacent the user's ears. The sensory device can convey audible information or other perceptible information (e.g., vibrations) to assist the user of the visualization device. For example, the sensory device may emit audible information resembling the sound a user hears when performing auscultation in-person.

Additionally, the output devices may include a haptic device configured to provide a haptic feedback based on the vibration data. In some examples, the haptic device may be a wearable glove including one or more haptic actuators configured to vibrate based on the vibration data. The haptic actuators may be arranged on the haptic device such that tactile stimuli provided by the haptic actuators resembles (e.g., in terms of intensity, location on the body part wearing the haptic device, etc.) the sensation a user experiences when performing palpation in-person.

By interacting with user interface 111 of computing system 110, the user may perform a remote examination of a patient in a manner similar, if not substantially similar to the performance of an in-person examination. For example, a user may wear the visualization device to view a virtual analog of medical device 102 being worn by a patient. In such an example, the user may select a virtual analog of a particular sensor (e.g., by contacting the virtual analog of the particular sensor with a virtual analog of the user's hands) to cause the appropriate output device or devices to output data associated with the selected sensor.

For example, the user may select a virtual analog of vibration sensor 105A of medical device 102 by moving the hand wearing the haptic device in the real-world such that the virtual analog of the haptic device is contacting (e.g., touching, proximate to, etc.) the virtual analog of vibration sensor 105A. Responsive to (and, optionally, only for the duration of) such contact between the virtual analogs, the haptic actuators of the haptic device may provide haptic feedback based on the portion of vibration data associated with vibration sensor 105A. The user may cause one or more sensory devices to output sound based on the portion of sound data associated with a particular sound sensor (e.g., sound sensor 103A) selected by the user in a similar manner.

Figure 2:
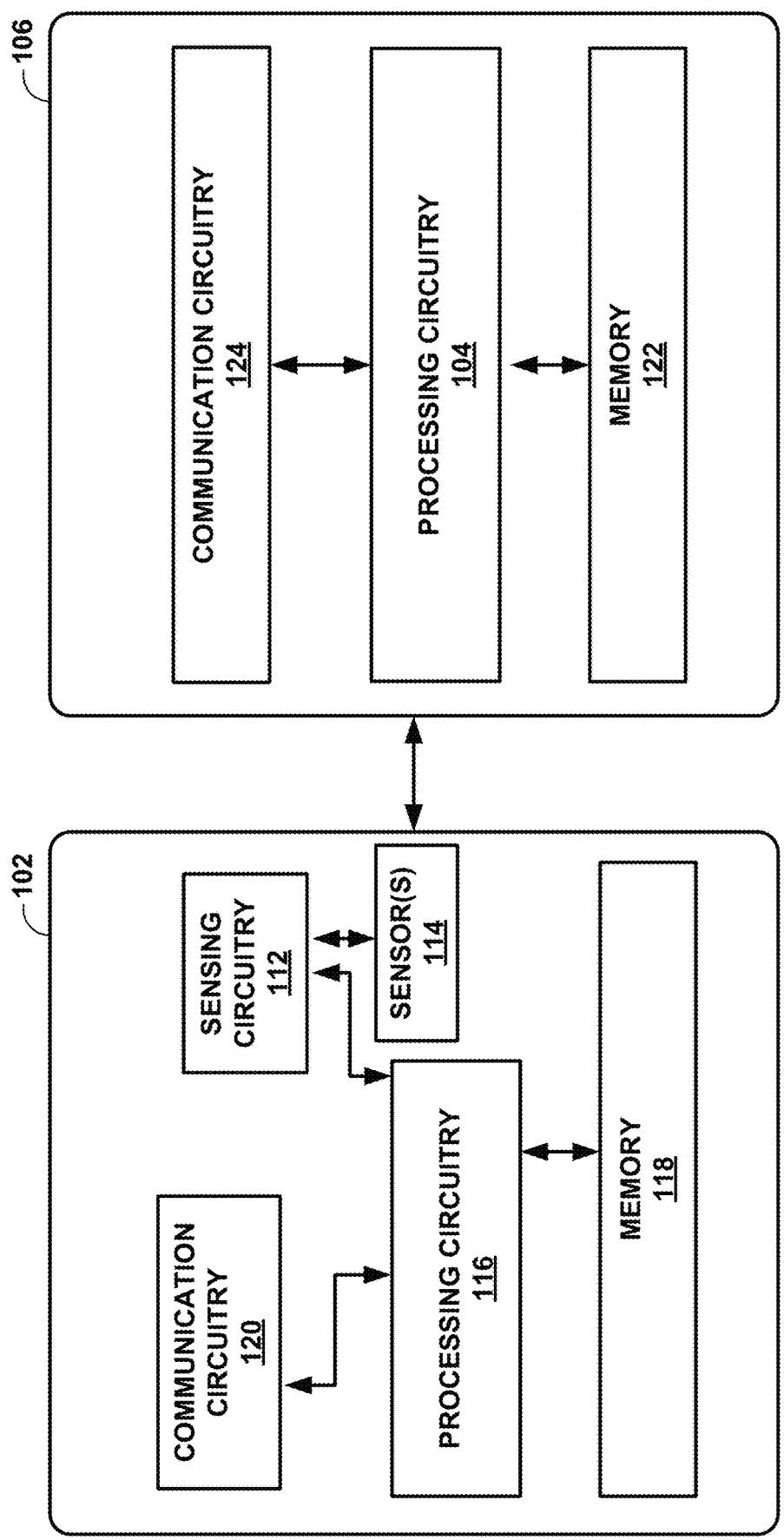
FIG. 2 is a functional block diagram illustrating an example configuration of an example medical device and external device of the system.

FIG. 2 is a functional block diagram illustrating an example configuration of example medical device 102 and external device 106 of system 100 of FIG. 1. As shown in FIG. 2, medical device 102 includes processing circuitry 116, sensing circuitry 112, communication circuitry 120, memory 118, and sensors 114. In some examples, memory 118 includes computer-readable instructions that, when executed by processing circuitry 116, cause medical device 102 and processing circuitry 116 to perform various functions attributed herein to medical device 102 and processing circuitry 116. Memory 118 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processing circuitry 116 may include fixed function circuitry and/or programmable processing circuitry. Processing circuitry 116 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 116 may include multiple components, such as any combination of one or more microprocessors, one or more controllers, one or more DSPs, one or more ASICs, or one or more FPGAs, as well as other discrete or integrated logic circuitry. The functions attributed to processing circuitry 116 herein may be embodied as software, firmware, hardware or any combination thereof.

Sensing circuitry 112 may be coupled to sensors 114 as controlled by processing circuitry 116. Sensing circuitry 112 may monitor signals from sensors 114 to monitor physiological parameters of a patient and produce sensor data for the patient. In some examples, processing circuitry 116 may store one or more segments of the sensor data in response to instructions from external device 106 (e.g., when the patient inputs a command to external device 106 instructing medical device 102 to upload the data for analysis by a monitoring center or clinician).

In some examples, processing circuitry 116 transmits, via communication circuitry 120, the episode data for the patient to an external device, such as external device 106 of FIG. 1. For example, medical device 102 sends digitized cardiac EGM and other episode data to a network for processing by computing system 110 of FIG. 1.

In some examples, medical device 102 may include a variety of sensors to collect sensor data. For example, sensors 114 may include sound sensors 103, vibration sensors 105, temperature sensors 107, pulse sensors 109, and/or other sensors configured to collect sensor data associated with one or more physiological parameters of a patient. Sensors 114 may be arranged with respect to medical device 102 such that sensors 114 may collect sensor data from various locations of the limb of the patient on which medical device 102 is positioned, in this way, assisting examination of a patient and, in turn, detection of a medical condition. Medical device 102 may be positioned such that one or more of sensors 114 are aligned (e.g., with proximal to) the AV access site.

In some examples, sensing circuitry 112 may include one or more filters and amplifiers for filtering and amplifying signals received from one or more of electrodes 16A, 16B and/or other sensors 114. In some examples, sensing circuitry 112 and/or processing circuitry 116 may include a rectifier, filter and/or amplifier, a sense amplifier, comparator, and/or analog-to-digital converter. Processing circuitry 116 may determine values of physiological parameters of the patient based on signals from sensors 114, which may be used to identify medical episodes and store sensor data associated with the identified episodes in memory 118.

Communication circuitry 120 may include any suitable hardware, firmware, software or any combination thereof for communicating with another device, such as external device 106. Under the control of processing circuitry 116, communication circuitry 120 may receive downlink telemetry from, as well as send uplink telemetry to, external device 106 or another device with the aid of an internal or external antenna. In some examples, processing circuitry 116 may communicate with a networked computing device via an external device (e.g., external device 106) and a computer network, such as the Medtronic CareLink® Network developed by Medtronic, plc, of Dublin, Ireland.

External device 106 is a computing device configured for wireless communication with medical device 102. For example, processing circuitry 104 may be configured to receive sensor data from medical device 102. As described above, external device 106 may be configured to communicate with medical device 102 via wired or wireless communication. As shown in FIG. 2, external device 106 includes processing circuitry 104, memory 122, and communication circuitry 124. In some examples, external device 106 may provide a user interface and allow a user to interact with medical device 102.

Processing circuitry 104 may include fixed function circuitry and/or programmable processing circuitry. Processing circuitry 104 may include any one or more of a microprocessor, a controller, a DSP, an ASIC, a FPGA, or equivalent discrete or analog logic circuitry. In some examples, processing circuitry 104 may include multiple components, such as any combination of one or more microprocessors, one or more controllers, one or more DSPs, one or more ASICs, or one or more FPGAs, as well as other discrete or integrated logic circuitry. The functions attributed to processing circuitry 104 herein may be embodied as software, firmware, hardware or any combination thereof.

Memory 122 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Communication circuitry 124 may include any suitable hardware, firmware, software or any combination thereof for communicating with another device, such as medical device 102, or system, such as computing system 110. In some examples, external device 106 may use communication circuitry 124 to communicate via NFC technologies and/or far-field communication technologies (e.g., RF telemetry according to the 802.11, Bluetooth® specification sets, or other communication technologies operable at ranges greater than NFC technologies. Additionally or alternatively, external device 102 may use communication circuitry 124 to communicate via a cellular radio, a 3G radio, a 4G radio, a 5G radio, or a WiFi® radio (or any other WLAN radio). The sensor data external device 106 receives from medical device 102 may include historical data stored to memory of medical device 102, and/or real-time data collected by medical device 102. Example types of sensor data may include sound data, vibration data, and other data about physiological parameters.

Figure 3:
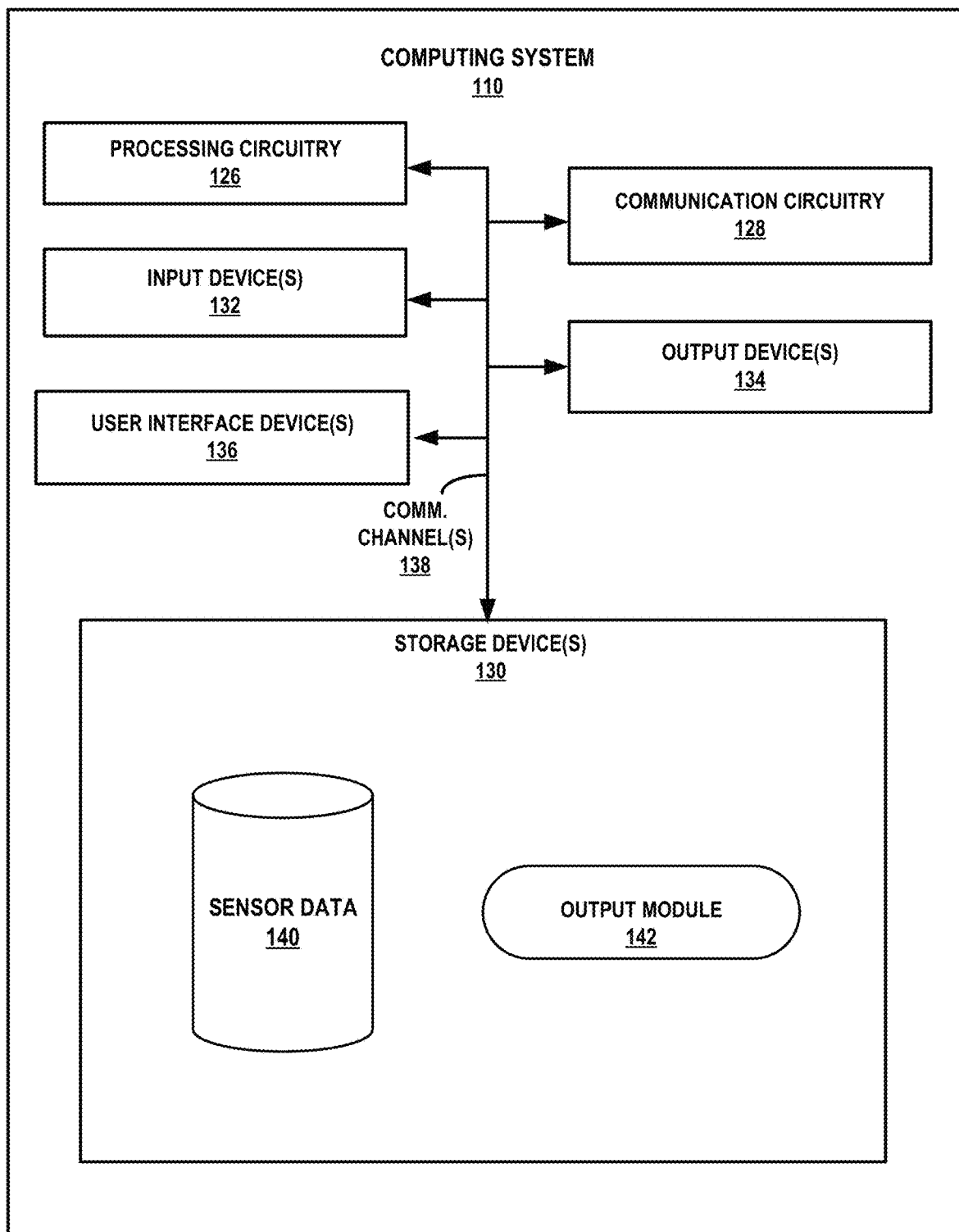
FIG. 3 is a functional block diagram illustrating an example configuration of an example computing system.

FIG. 3 is a block diagram illustrating an example configuration of computing system 110. In the illustrated example, computing system 110 includes processing circuitry 126 for executing an output module 142. Computing system 110 may be any component or system that includes processing circuitry or other suitable computing environment for executing software instructions and, for example, need not necessarily include one or more elements shown in FIG. 3 (e.g., communication circuitry 128, input devices 132, output devices 134, or user interface devices 136; and in some examples components such as storage device(s) 130 may not be co-located or in the same chassis as other components). In some examples, computing system 110 may be a cloud computing system distributed across a plurality of devices.

In the example of FIG. 3, computing system 110 includes processing circuitry 126, one or more input devices 132, communication circuitry 128, one or more storage devices 130, user interface (UI) device(s) 136, and one or more output devices 134. Each of components 126, 128, 130, 132, 134, and 136 may be coupled (physically, communicatively, and/or operatively) for inter-component communications. In some examples, communication channels 138 may include a system bus, a network connection, an inter-process communication data structure, or any other method for communicating data. As one example, components 126, 128, 130, 132, 134, and 136 may be coupled by one or more communication channels 138.

Processing circuitry 126, in one example, is configured to implement functionality and/or process instructions for execution within computing system 110. For example, processing circuitry 126 may be capable of processing instructions stored in storage device 130. Examples of processing circuitry 126 may include any one or more of a microprocessor, a controller, a digital signal processor (DSP), an application specific integrated circuit (ASIC), a field-programmable gate array (FPGA), or equivalent discrete or integrated logic circuitry.

Storage device 130, in some examples, is described as a computer-readable storage medium. In some examples, storage device 130 is a temporary memory, meaning that a primary purpose of storage device 130 is not long-term storage. Storage device 130, in some examples, is described as a volatile memory, meaning that storage device 130 does not maintain stored contents when the computer is turned off. Examples of volatile memories include RAM, dynamic random access memories (DRAM), static random access memories (SRAM), and other forms of volatile memories known in the art. In some examples, storage device 130 is used to store program instructions for execution by processing circuitry 126. Storage device 130, in one example, is used by output module 142 running on computing system 110 to temporarily store information during program execution.

Storage devices 130, in some examples, also include one or more computer-readable storage media. Storage devices 130 may be configured to store larger amounts of information than volatile memory. Storage devices 130 may further be configured for long-term storage of information. In some examples, storage devices 130 include non-volatile storage elements. Examples of such non-volatile storage elements include magnetic hard discs, optical discs, floppy discs, flash memories, or forms of electrically programmable memories (EPROM) or electrically erasable and programmable memories (EEPROM).

Computing system 110, in some examples, also includes communication circuitry 128 to communicate with other devices and systems, such as medical device 102 and external device 106 of FIG. 1. Communication circuitry 128 may include a network interface card, such as an Ethernet card, an optical transceiver, a radio frequency transceiver, or any other type of device that can send and receive information. Other examples of such network interfaces may include 3G, 4G, 5G, and WiFi radios.

Computing system 110, in one example, also includes one or more user interface devices 136. User interface devices 136, in some examples, are configured to receive input from a user through tactile, audio, or video feedback. Examples of user interface devices(s) 136 include a visualization device, a presence-sensitive display, a mouse, a keyboard, a voice responsive system, video camera, microphone or any other type of device for detecting a command from a user. In some examples, a presence-sensitive display includes a touch-sensitive screen.

One or more output devices 134 may also be included in computing system 110. Output devices 134, in some examples, are configured to provide output to a user using tactile, audio, or video stimuli. Output devices 134, in one example, include a presence-sensitive display, a sound card, a video graphics adapter card, or any other type of device for converting a signal into an appropriate form understandable to humans or machines. Additional examples of output devices 134 include a speaker, a cathode ray tube (CRT) monitor, a liquid crystal display (LCD), or any other type of device that can generate intelligible output to a user. In some examples, output devices 134 may include one or more of user interface devices 136, such as a visualization device. That is, some user interface devices 136 may include both input and output components, such that user interface devices 136 may be both input devices 132 and output devices 134.

In accordance with the techniques of the disclosure, computing system 110 receives sensor data for episodes stored by medical devices, such as medical device 102, via communication circuitry 128. Storage device 130 may store the sensor data in sensor data repository 140 of storage device 130. Output module 142 may be configured to control output devices 134 based on the sensor data stored in sensor data repository 140. For example, output module 142 may cause one or more sensory devices to emit sound based on sound data, one or more haptic devices to provide haptic feedback based on vibration data, a display (e.g., that may or may not be built into the visualization device) to display metrics based on pulse data, temperature data, etc. In some examples, output module 142 may cause output devices 134 to provide output based on sensor data associated with a particular sensor selected by a user. In some examples, the user may select a virtual analog of the particular sensor in a virtual reality while wearing the visualization device. Responsive to a particular sensor being selected, output module 142 may cause output devices 134 to output audio, tactile, and/or other stimuli based on the sensor data associated with the selected sensor (but not the unselected sensors).

Figure 4:
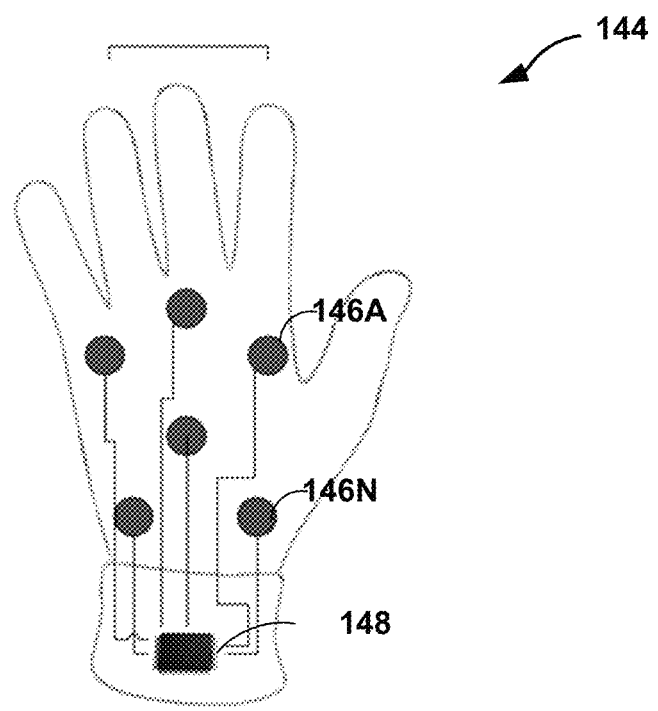
FIG. 4 is a conceptual diagram of an example output device configured to provide haptic feedback.

FIG. 4 is a conceptual diagram of a haptic device 144 configured to perform techniques in accordance with this disclosure. As shown in FIG. 4, haptic device 144 is a wearable glove including one or more haptic actuators 146A-146N (collectively, "haptic actuators 146") and processing circuitry 148. Haptic device 144 is an example of user interface devices 136.

Haptic device 144 may be configured to output tactile stimuli based on sensor data stored in sensor data repository 140. For example, computing system 110 may transmit sensor data stored in sensor data repository 140 to haptic device 144 via communication channels 138. The sensor data may include vibration data. In some examples, haptic device 144 may provide haptic feedback based on the vibration data and, in particular, the vibration data associated with a selected vibration sensor of medical device 102. In general, the haptic feedback produced by haptic actuators 146 may approximate real-world tactile stimuli perceived by a physician or other person when performing palpation during an in-person examination.

In some examples, processing circuitry 148 of haptic device 144 may selectively operate one or more of haptic actuators 146 to produce haptic feedback based on whether a virtual analog of the one or more haptic actuators 146 is in contact with the virtual analog of one or more sensors of medical device 102. For example, if a user of haptic device 144 moves the hand wearing haptic device 144 such that, in the virtual reality produced by a visualization device, a virtual analog of haptic actuator 146A is in contact with a virtual analog of a particular vibration sensor of medical device 102 (in this way selecting the particular vibration sensor), then haptic actuator 146A may produce haptic feedback based on the vibration data associated with the selected vibration sensor. The haptic feedback outputted by haptic actuator 146A may be configured to be similar, if not substantially similar, to tactile stimuli the user would perceive when touching the limb of the patient wearing medical device 102 where the selected vibration sensor is located. Haptic actuators 146 with virtual analogs that are not in contact with virtual analogs of vibration sensors of medical device 102 may not produce any haptic feedback.

Figure 5:
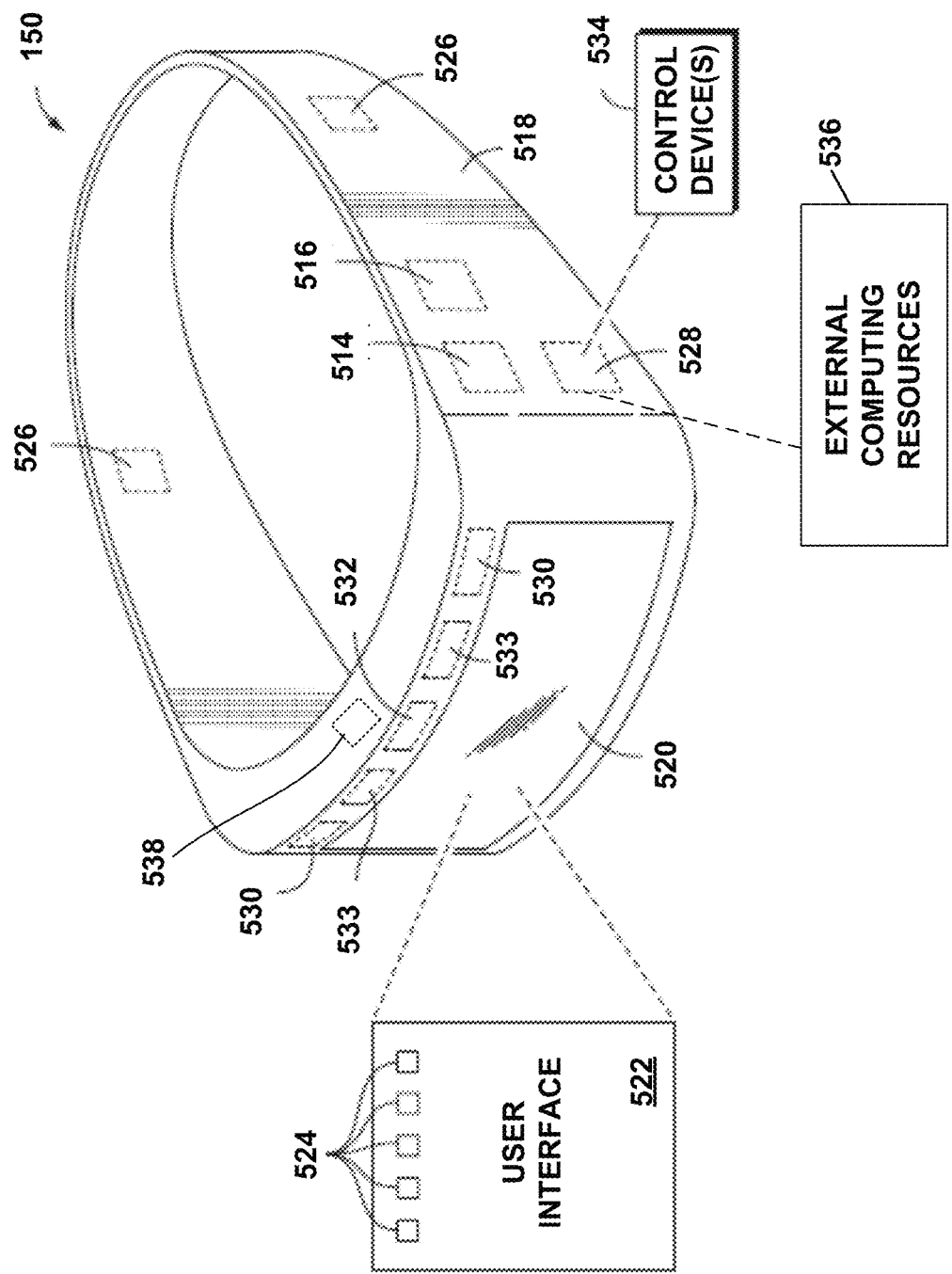
FIG. 5 is a conceptual diagram of a visualization device for use in an augmented reality (AR) system, according to an example of this disclosure.

FIG. 5 is a conceptual diagram of a visualization device 150 for use in a medical system, such as medical system 100 of FIG. 1, according to techniques of this disclosure. Visualization device 150 may enable a user to manipulate a GUI when wearing visualization device 150 to select a virtual analog of a particular sensor (e.g., temperature sensor 107A) of medical device 102 to trigger output, via one or more output devices 134, of a portion of the sensor data collected by the particular sensor. As shown in the example of FIG. 5, visualization device 150 can include a variety of electronic components found in a computing system, including one or more processor(s) 514 (e.g., microprocessors or other types of processing units) and memory 516 that may be mounted on or within a frame 518. Furthermore, in the example of FIG. 5, visualization device 150 may include a transparent screen 520 that is positioned at eye level when visualization device 150 is worn by a user. In some examples, screen 520 can include one or more liquid crystal displays (LCDs) or other types of display screens on which images are perceptible to a surgeon who is wearing or otherwise using visualization device 150 via screen 520. Other display examples include organic light emitting diode (OLED) displays. In some examples, visualization device 150 can operate to project 3D images onto the user's retinas using techniques known in the art.

In some examples, screen 520 may include see-through holographic lenses. sometimes referred to as waveguides, that permit a user to see real-world objects through (e.g., beyond) the lenses and also see holographic imagery projected into the lenses and onto the user's retinas by displays, such as liquid crystal on silicon (LCoS) display devices, which are sometimes referred to as light engines or projectors, operating as an example of a holographic projection system 538 within visualization device 150. In other words, visualization device 150 may include one or more see-through holographic lenses to present virtual images to a user. Hence, in some examples, visualization device 150 can operate to project 3D images onto the user's retinas via screen 520, e.g., formed by holographic lenses. In this manner, visualization device 150 may be configured to present a 3D virtual image to a user within a real-world view observed through screen 520, e.g., such that the virtual image appears to form part of the real-world environment. In some examples, visualization device 150 may be a MR visualization device that includes waveguides. Such a visualization device, and other visualization devices, can be used to present 3D virtual objects via holographic lenses, or waveguides, while permitting a user to view actual objects in a real-world scene, i.e., in a real-world environment, through the holographic lenses.

Although the example of FIG. 5 illustrates visualization device 150 as a head-wearable device, visualization device 150 may have other forms and form factors. For instance, in some examples, visualization device 150 may be a handheld smartphone or tablet.

Visualization device 150 can also generate a graphical user interface 522 ("GUI 522") that is visible to the user, e.g., as holographic imagery projected into see-through holographic lenses as described above. For example, GUI 522 can include a variety of selectable widgets 524 that allow the user to interact with a mixed reality (MR) system, such as medical system 100. Imagery presented by visualization device 150 may include, for example, one or more 3D virtual objects. Visualization device 150 also can include a speaker or other sensory devices 526 that may be positioned adjacent the user's ears. Sensory devices 526 can convey audible information or other perceptible information (e.g., vibrations) to assist the user of visualization device 150.

Visualization device 150 can also include a transceiver 528 to connect visualization device 150 to a processing device 510 and/or to communication channels 138 and/or to a network and/or to a computing cloud, such as via a wired communication protocol or a wireless protocol, e.g., Wi-Fi, Bluetooth, etc. Visualization device 150 also includes a variety of sensors to collect sensor data, such as one or more optical camera(s) 530 (or other optical sensors) and one or more depth camera(s) 532 (or other depth sensors), mounted to, on or within frame 518. In some examples, the optical sensor(s) 530 are operable to scan the geometry of the physical environment in which user of medical system 100 is located (e.g., an examination room) and collect two-dimensional (2D) optical image data (either monochrome or color). Depth sensor(s) 532 are operable to provide 3D image data, such as by employing time of flight, stereo or other known or future-developed techniques for determining depth and thereby generating image data in three dimensions. Other sensors can include motion sensors 533 (e.g., Inertial Mass Unit (IMU) sensors, accelerometers, etc.) to assist with tracking movement.

Visualization device 150 may process the sensor data so that geometric, environmental, textural, etc. landmarks (e.g., corners, edges or other lines, walls, floors, objects) in the user's environment or "scene" can be defined and movements within the scene can be detected. As an example, the various types of sensor data can be combined or fused so that the user of visualization device 150 can perceive 3D images that can be positioned, or fixed and/or moved within the scene. When fixed in the scene, the user can walk around the 3D image, view the 3D image from different perspectives, and manipulate the 3D image within the scene using hand gestures, voice commands, gaze line (or direction) and/or other control inputs. As another example, the sensor data can be processed so that the user can position a 3D virtual object (e.g., an anatomical model) on an observed physical object in the scene (e.g., a surface, etc.) and/or orient the 3D virtual object with other virtual images displayed in the scene.

Visualization device 150 may include one or more processors 514 and memory 516, e.g., within frame 518 of the visualization device. In some examples, one or more external computing resources 536 process and store information, such as sensor data, instead of or in addition to in-frame processor(s) 514 and memory 516. In this way, data processing and storage may be performed by one or more processors 514 and memory 516 within visualization device 150 and/or some of the processing and storage requirements may be offloaded from visualization device 150. Hence, in some examples, one or more processors that control the operation of visualization device 150 may be within the visualization device, e.g., as processor(s) 514. Alternatively, in some examples, at least one of the processors that controls the operation of visualization device 150 may be external to the visualization device, e.g., as processor(s) 126. Likewise, operation of visualization device 150 may, in some examples, be controlled in part by a combination one or more processors 514 within the visualization device and one or more processors 126 external to the visualization device.

For instance, in some examples, when visualization device 150 is in the context of FIG. 3, processing of the sensor data can be performed by processing device(s) 126 in conjunction with memory or storage device(s) 130. In some examples, processor(s) 514 and memory 516 mounted to frame 518 may provide sufficient computing resources to process the sensor data collected by cameras 530, 532 and motion sensors 533. In some examples, the sensor data can be processed using a Simultaneous Localization and Mapping (SLAM) algorithm, or other known or future-developed algorithm for processing and mapping 2D and 3D image data and tracking the position of visualization device 150 in the 3D scene. In some examples, image tracking may be performed using sensor processing and tracking functionality provided by systems known in the art.

In some examples, medical system 100 can also include user-operated control device(s) 534 that allow the user to operate visualization device 150, interact with GUI 522 and/or otherwise provide commands or requests to processing device(s) 126 or other systems connected to computing system 110 (e.g., via communication channels 138). As examples, the control device(s) 534 can include a microphone, a touch pad, a control panel, a motion sensor or other types of control input devices with which the user can interact. One or more of control devices 534 may be input devices 132.

Figure 6:
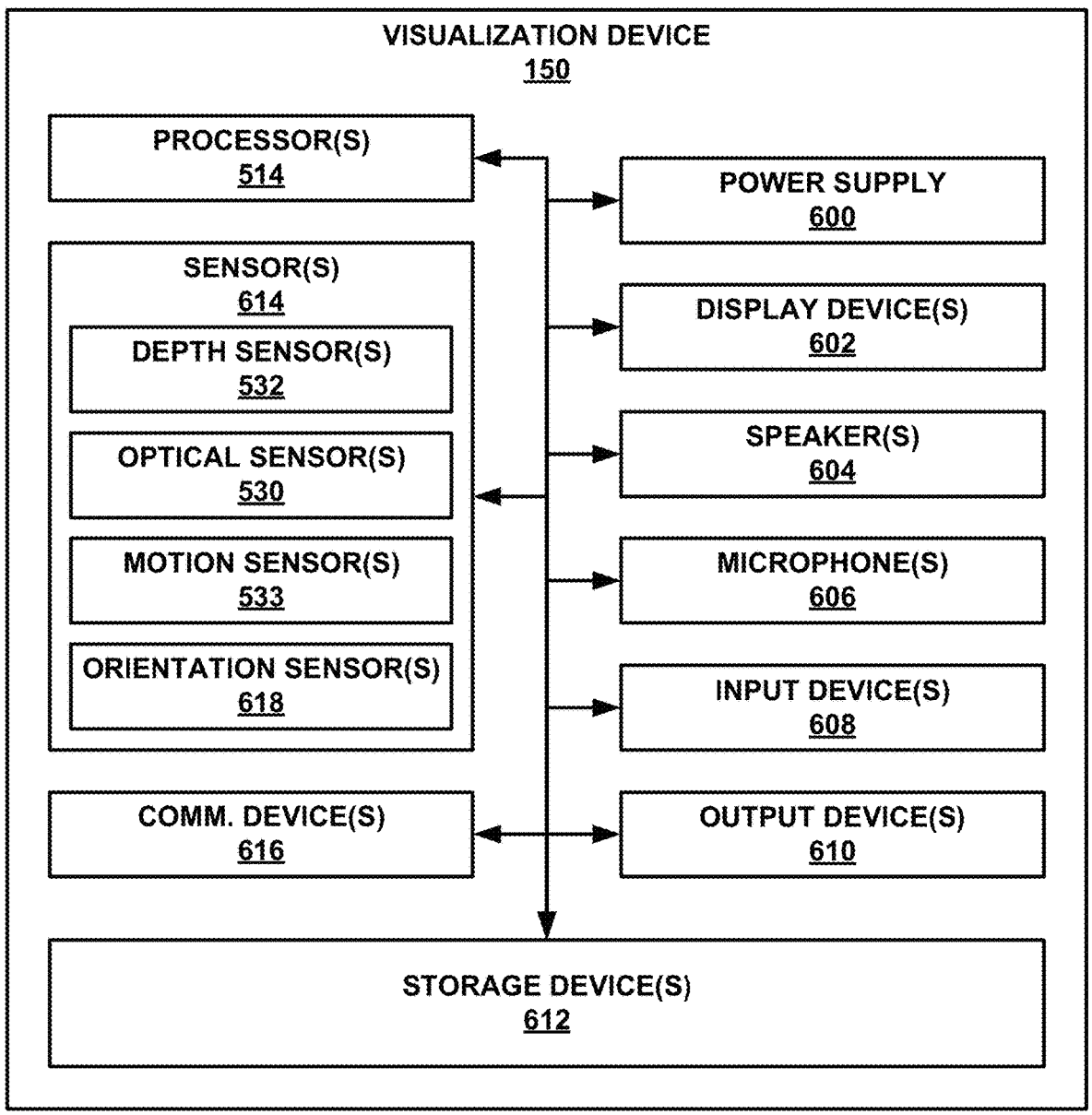
FIG. 6 is a block diagram illustrating example components of a visualization device for use in an augmented reality (AR) system, according to an example of this disclosure.

FIG. 6 is a block diagram illustrating example components of visualization device 150. In the example of FIG. 6, visualization device 150 includes processors 514, a power supply 600, display device(s) 602, speakers 604, microphone(s) 606, input device(s) 608, output device(s) 610, storage device(s) 612, sensor(s) 614, and communication devices 616. In the example of FIG. 6, sensor(s) 616 may include depth sensor(s) 532, optical sensor(s) 530, motion sensor(s) 533, and orientation sensor(s) 618. Optical sensor(s) 530 may include cameras, such as Red-Green-Blue (RGB) video cameras, infrared cameras, or other types of sensors that form images from light. Display device(s) 602 may display imagery to present a user interface to the user.

Speakers 604, in some examples, may form part of sensory devices 526 shown in FIG. 5. In some examples, display devices 602 may include screen 520 shown in FIG. 5. For example, as discussed with reference to FIG. 5, display device(s) 602 may include see-through holographic lenses, in combination with projectors, that permit a user to see real-world objects, in a real-world environment, through the lenses, and also see virtual 3D holographic imagery projected into the lenses and onto the user's retinas, e.g., by a holographic projection system. In this example, virtual 3D holographic objects may appear to be placed within the real-world environment. In some examples, display devices 602 include one or more display screens, such as LCD display screens, OLED display screens, and so on. The user interface may present virtual images of details of the virtual surgical plan for a particular patient.

In some examples, a user may interact with and control visualization device 150 in a variety of ways. For example, microphones 606, and associated speech recognition processing circuitry or software, may recognize voice commands spoken by the user and, in response, perform any of a variety of operations, such as selection, activation, or deactivation of various functions associated with examining physiological parameters of a patient or the like. As another example, one or more cameras or other optical sensors 530 of sensors 614 may detect and interpret gestures to perform operations as described above. For example, optical sensors 530 may detect hand movements by the user of visualization device 150 such that visualization device 150 may simulate those hand movements using the virtual analogs of the user's hands in the virtual reality. As a further example, sensors 614 may sense gaze direction and perform various operations as described elsewhere in this disclosure. In some examples, input devices 608 may receive manual input from a user, e.g., via a handheld controller including one or more buttons, a keypad, a touchscreen, joystick, trackball, and/or other manual input media, and perform, in response to the manual user input, various operations as described above.

Figure 7:
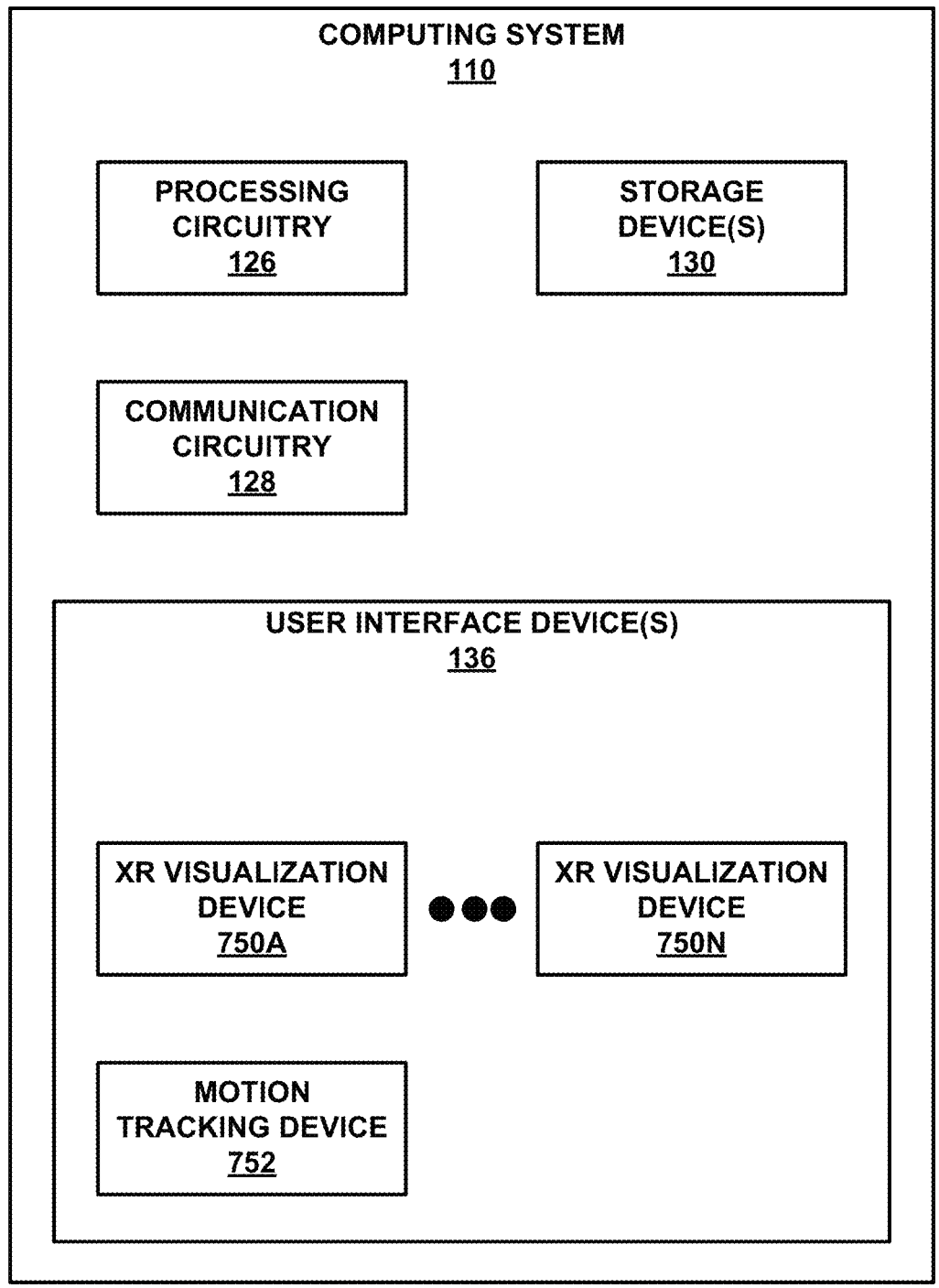
FIG. 7 is block diagram illustrating an example system for generating an extended reality visualization, in accordance with a technique of this disclosure.

FIG. 7 is block diagram illustrating medical system 100 including one or more components configured to generate an extended reality (e.g., augmented reality, virtual reality, mixed reality, etc.) visualization of a medical device being worn on an appendage of a user, in accordance with techniques of this disclosure. As shown in the example of FIG. 7, system 100 includes computing system 110, a set of one or more extended reality (XR) visualization devices 750A through 750N (collectively, "XR visualization devices 750"), and a motion tracking device 752. In other examples, system 100 may include more, fewer, or different devices and systems. In some examples, computing system 110, XR visualization devices 750, and motion tracking device 752 may communicate via one or more communication networks, such as the Internet.

Computing system 110 may include various types of computing devices, such as server computers, personal computers, smartphones, laptop computers, and other types of computing devices. In the example of FIG. 7, computing system 110 includes one or more processing circuits 126, communication circuitry 128, and one or more storage devices 130. Storage device 130 is configured to store data, such as motion data. Communication circuitry 128 may enable computing system 110 to communicate (e.g., wirelessly or using wires) to other computing systems and devices, such as XR visualization devices 750 and motion tracking device 752. For ease of explanation, this disclosure may describe actions performed by processing circuitry 126, storage device 130, and communication circuitry 128 as being performed by computing system 110 as a whole.

In some examples, one or more of XR visualization devices 750 include one or more components of computing system 110. For instance, one or more of XR visualization devices 750 may include one or more of processing circuits 126 of computing system 110. Thus, in some examples, some or all of the actions described in this disclosure as being performed by computing system 110 may be performed by processing circuits in one or more of XR visualization devices 750. In some examples, XR visualization devices 750 include MR visualization devices, such as MR visualization device 150 (FIG. 5). In some examples, XR visualization devices 750 include VR visualization devices, AR visualization devices, etc.

Motion tracking device 752 is a device configured to detect movement. For instance, in some examples, motion tracking device 752 may include a device that is connected to an appendage of the user of XR visualization devices 750 and detects movement of motion tracking device 752. Motion tracking device 752 may, for example, be a device having an inertial measurement unit (IMU) that tracks acceleration of motion tracking device 752 in multiple dimensions (e.g., 3 dimensions). In some examples, the IMU may also track an orientation of motion tracking device 752 (e.g., with respect to a gravitational vector or a magnetic pole). Motion tracking device 752 may be or may include various types of devices. For example, motion tracking device 752 may be or may include a smartwatch, a smartphone, a ring, a bracelet, an anklet, a head-mounted device, eyewear, a special-purpose motion tracking device, or another type of device configured to detect movement of the device.

In examples where motion tracking device 752 is or includes a device that is connected to the appendage of the user and detects movement of motion tracking device 752, motion tracking device 752 may be connected to the appendage in various ways. For instance, motion tracking device 752 may be connected to a wrist, ankle, thigh, toe, finger, head, knee, calf, upper arm, hand, jaw, or other body part of the user. Motion tracking device 752 may be connected to the appendage in various ways. For example, motion tracking device 752 may be held by the user (e.g., as may be the case when the user holds motion tracking device 752 in one of the user's hands); may be strapped to the user (e.g., as may be the case when motion tracking device 752 is worn on the user's wrist or ankle); may be attached with adhesive, may rest on the user due to gravity and/or compression (e.g., as may be the case when motion tracking device 752 includes eyewear or headwear); may be held in place by compression (e.g., as may be the case when motion tracking device 752 is worn as a ring or clamp; or in may connected to the appendage of the user in other ways such that motion tracking device 752 moves with the appendage of the user. In some examples, motion tracking device 752 may instruct the user to start a movement at a calibration position (e.g., arm straight down) and track movements relative to the calibration position.

In some examples, motion tracking device 752 may include one or more cameras or other devices that visually detect the movement of the appendage. For instance, in some examples, one or more cameras may be integrated into an XR visualization device worn by the user. In some examples where the one or more cameras are integrated into an XR visualization device worn by the user, the user may need to be positioned in front of a mirror so that the camera is able to capture images of the movement of the appendage of the user.

In accordance with an example of this disclosure, computing system 110 may obtain motion data describing a movement of an appendage of a user. For example, computing system 110 may obtain motion data that include IMU signals generated by an IMU of motion tracking device 752 during the movement of the appendage of the user. In some examples, computing system 110 may obtain video data that show the movement of the appendage of the user. In some examples, a storage system (e.g., storage devices 130, etc.) may store the motion data.

In some examples, the user of one or more of XR visualization devices 750 may be a physician or other healthcare professional, such as a nurse. That is, XR visualization devices may present the extended reality visualization of medical device 102 being worn by the patient, including sensors of medical device 102, and associated sensor data to one or more healthcare professionals, such as doctors, surgeons, or nurses. For example, a physician and a patient may engage in an interactive session during which the healthcare professional wears or otherwise uses one or more XR visualization devices 750. In this example, the physician and the patient may be in separate locations. In other words, an XR visualization device may present the extended reality visualization to the healthcare professional during an interactive session with the user in which the healthcare professional and the user are in separate locations, as may be the case during a telemedicine session.

In some examples where the extended reality visualization is presented to a healthcare professional, the healthcare professional views the extended reality visualization outside the context of an interactive session with the user. In other words, an XR visualization device may present the extended reality visualization to a healthcare professional during a session in which the user is not involved. For example, the user may select various sensors of medical device 102 to cause one or more output devices 134 (including XR visualization devices 750) to output tactile, audio, and other stimuli based on sensor data collected by the selected sensors of medical device 102.

Figure 8:
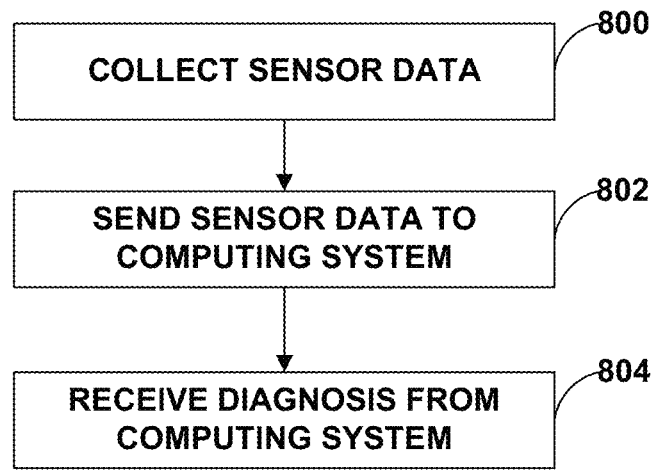
FIG. 8 is a flowchart illustrating an exemplary operation of a medical device in accordance with at least one technique disclosed herein.

FIG. 8 is a flow diagram illustrating an example method for performing a remote inspection of a patient, particularly in order to diagnose a patient for stenosis and/or thrombosis. Although FIG. 8 is discussed primarily in the context of medical system 100 of FIG. 1, it should be understood that the method of FIG. 8 may be applied to other examples of medical systems as described herein.

Medical device 102 of medical system 100 may collect sensor data based on signals from sensors 114 of medical device 102 (800). In some examples, medical device 102 may include sound sensors 103, vibration sensors 105 (e.g., accelerometers, piezoelectric sensors, etc.), temperature sensors 107 (e.g., thermocouples, resistance temperature detectors, etc.), pulse sensors 109 (e.g., oximeters), and/or other sensors configured to collect sensor data associated with one or more physiological parameters of a patient. Sensors 114 may be arranged such that sensors 114 may collect sensor data from a variety of locations on the limb of a patient, which may assist detection of a medical condition. In some examples, medical device 102 may be positioned such that one or more of sensors 114 are aligned with the AV access site.

External device 106, such as a computing device (e.g., a smartphone, a tablet computer, a laptop, etc.), may include processing circuitry 104 configured to receive sensor data from medical device 102. For example, external device 106 may communicate with medical device 102 via wired or wireless communication. The sensor data external device 106 receives from medical device 102 may include historical data stored to memory of medical device 102, and/or real-time data collected by medical device 102. Example types of sensor data may include sound data, vibration data, and other data about physiological parameters.

Responsive to collecting the sensor data, processing circuitry 104 may evaluate the sensor data and, based on the evaluation of the sensor data, send at least a portion of the sensor data to computing system 110. For example, processing circuitry 104 may be configured to process the sensor data to determine whether a risk of the occurrence of at least one of stenosis or thrombosis exceeds a respective threshold risk for each of those conditions. That is, processing circuitry 104 may be configured to process the sensor data to determine whether a risk of the occurrence of the at least one of the stenosis or the thrombosis exceeds a threshold risk of the occurrence of the at least one of the stenosis or the thrombosis. As an example, processing circuitry 104 may evaluate a risk of occurrence of stenosis or thrombosis based on the difference between the current levels of various physiological parameters (e.g., temperature, pulse, etc.) and baseline levels (e.g., the average levels for a particular patient during a prior time period) of those various physiological parameters.

In some examples, the algorithm executed by processing circuitry 104 may involve evaluating the morphology of sensor data in the detection and discrimination of AV fistula dysfunction. In some examples, processing circuitry 104 may use a template comparison algorithm to compare the sensor data to template sensor data corresponding to a predetermined template. Based on the template comparisons, processing circuitry 104 may classify the sensor data as indicative of AV fistula dysfunction and send the sensor data to computing system 110. For example, processing circuitry 104 may compare a portion of audio data collected during a session to template audio data indicative of one or more of stenosis or thrombosis. In such an example, processing circuitry 104 may use audio processing techniques known in the art to compare the waveform of the portion of audio data collected during the session to the waveform of the template audio data.

Processing circuitry 104 may transmit the sensor data to computing system via network 108 (802). Computing system may be configured to receive the sensor data from processing circuitry 104 and to output the sensor data via user interface 111 (which includes user interface devices 136) including one or more output devices 134. In some examples, output devices 134 are configured to provide output to a user using video, tactile, and/or audio stimuli. An example output device 134 is visualization device 150. In some examples, visualization device 150 is wearable by a user. In some examples, visualization device 150 is held by a user, or rests on a surface in a place accessible to the user. Visualization device 150 may present a GUI that is visually perceptible to the user using visualization device 150. For instance, in one example, a screen of visualization device 150 may display real-world images and the GUI on a screen. The GUI may be configured to include, for example, temperature data, pulse data, and other sensor data indicative of the physiological parameters of the patient in a manner comprehensible to a user (e.g., as indicators, diagrams, metrics, etc.).

In some examples, visualization device 150 may project virtual, holographic images onto see-through holographic lenses and also permit a user to see real-world objects of a real-world environment through the lenses. In other words, visualization device 150 may include one or more see-through holographic lenses and one or more display devices that present imagery to the user via the holographic lenses to present the GUI to the user.

Output devices 134 may include a speaker or other sensory device configured to output sound based on the sound data. In some examples, visualization device 150 may include such a sensory device, which may be positioned adjacent the user's ears. The sensory device can convey audible information or other perceptible information (e.g., vibrations) to assist the user of visualization device 150. For example, the sensory device may emit audible information resembling the sound a user hears when performing auscultation in-person.

Additionally, output devices 134 may include haptic device 144 configured to provide a haptic feedback based on the vibration data. In some examples, haptic device 144 may be a wearable glove including one or more haptic actuators configured to vibrate based on the vibration data. The haptic actuators may be arranged on haptic device 144 such that tactile stimuli provided by the haptic actuators resembles (e.g., in terms of intensity, location, etc.) the sensation a user experiences when performing palpation in-person.

By interacting with user interface 111 of computing system 110, the user may perform a remote examination of a patient in a manner similar, if not substantially similar to the performance of an in-person examination. For example, a user may wear visualization device 150 to view a virtual analog of medical device 102 being worn by a patient. In such an example, the user may select a virtual analog of a particular sensor (e.g., by contacting the virtual analog of the particular sensor with a virtual analog of the user's hands) to cause corresponding output device 134 or devices to output data associated with the selected sensor. As a result, the user may diagnose the patient wearing medical device 102 concerning stenosis, thrombosis, and/or other medical conditions. The user may input the diagnosis into computing system 110 (e.g., via a keyboard, via a microphone being used in a telemedicine session). Computing system 110 may then transmit the diagnosis to external device 106 or some other computing device owned by the patient via network 108. That is, external device 106 (or some other computing device in communication with computing system 110) may receive the diagnosis from computing system 110 (804).

Figure 9:
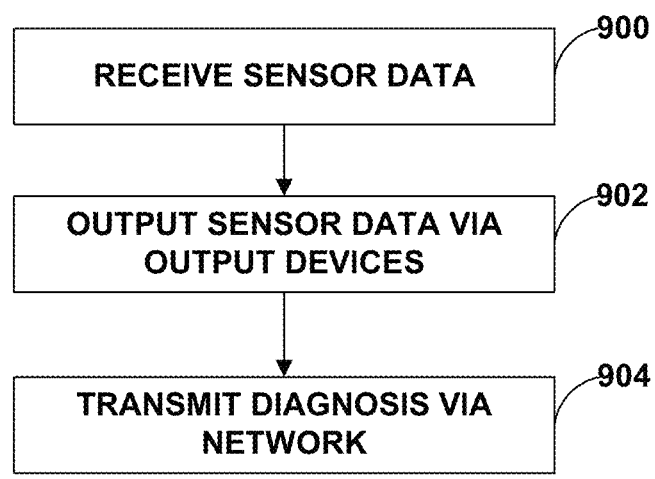
FIG. 9 is a flowchart illustrating an exemplary operation of a computing system and one or more output devices in accordance with at least one technique disclosed herein.

FIG. 9 is a flow diagram illustrating an example method for performing a remote inspection of a patient, particularly in order to diagnose a patient for stenosis or thrombosis. Although FIG. 9 is discussed primarily in the context of computing system 110 of FIG. 3, it should be understood that the method of FIG. 9 may be applied to other examples of medical systems as described herein.

Computing system 110 may receive sensor data from external device 106 via network 108 (900). Storage device 130 may store the sensor data in sensor data repository 140. Output module 142 may be configured to control output devices 134 based on the sensor data stored in sensor data repository 140 (902). For example, output module 142 may cause one or more output devices 134 to emit sound based on sound data, one or more haptic devices 144 to provide haptic feedback based on vibration data, a display (e.g., that may or may not be built into the visualization device) to display metrics based on pulse data, temperature data, etc. In some examples, output module 142 may cause output devices 134 to provide output based on sensor data associated with a particular sensor selected by a user.

In some examples, output devices 134 may include one or more of user interface devices 136, such as visualization device 150. In such examples, the user may select a virtual analog of the particular sensor in a virtual reality while wearing visualization device 150. Responsive to a particular sensor being selected, output module 142 may cause output devices 134 to output audio, tactile, and/or other stimuli based on the sensor data associated with the selected sensor (but not the unselected sensors).

The user of user interface 111 of computing system 110 may diagnose the patient based on the output provided by output devices 134 and/or user interface devices 136. For example, the user may diagnose (e.g., based on the haptic feedback provided by haptic device 144 based on vibration data, the sound produced by speakers 604 based on sound data, etc.) the patient wearing medical device 102 concerning stenosis, thrombosis, and/or other medical conditions. The user may input the diagnosis into computing system 110 (e.g., via a keyboard, via a microphone being used in a telemedicine session). Computing system 110 may then transmit the diagnosis to external device 106 or some other computing device owned by the patient via network 108.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

Based upon the above discussion and illustrations, it is recognized that various modifications and changes may be made to the disclosed technology in a manner that does not necessarily require strict adherence to the examples and applications illustrated and described herein. Such modifications do not depart from the true spirit and scope of various aspects of the disclosure, including aspects set forth in the claims.

In at least one example, the functions described may be implemented in hardware, software, firmware, or any combination thereof. If implemented in software, the functions may be stored on or transmitted over as at least one instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by at least one computers or at least one processors to retrieve instructions, code and/or data structures for implementation of the techniques described in this disclosure. A computer program product may include a computer-readable medium.

By way of example, and not limitation, such computer-readable data storage media can include RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Combinations of the above should also be included within the scope of computer-readable media.

Instructions may be executed by at least one processors, such as at least one DSPs, general purpose microprocessors, ASICs, FPGAs, CPLDs, or other equivalent integrated or discrete logic circuitry. Accordingly, the term "processor," as used herein may refer to any of the foregoing structure or any other structure suitable for implementation of the techniques described herein. Also, the techniques could be fully implemented in at least one circuits or logic elements.

Any of the above-mentioned "processors," and/or devices incorporating any of the above-mentioned processors or processing circuitry, may, in some instances, be referred to herein as, for example, "computers," "computer devices," "computing devices," "hardware computing devices," "hardware processors," "processing units," "processing circuitry," etc. Computing devices of the above examples may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In some examples, the computing devices may be controlled by a proprietary operating system. Conventional operating systems control and schedule computer processes for execution, perform memory management, provide file system, networking, I/O services, and provide UI functionality, such as GUI functionality, among other things.

The techniques of this disclosure may be implemented in a wide variety of devices or apparatuses, including an integrated circuit (IC) or a set of ICs (e.g., a chip set). Various components, modules, or units are described in this disclosure to emphasize functional aspects of devices configured to perform the disclosed techniques, but do not necessarily require realization by different hardware units.

In this disclosure, the term "mixed reality" (MR) refers to the presentation of virtual objects such that a user sees images that include both real, physical objects and virtual objects. Virtual objects may include text, 2-dimensional surfaces, 3-dimensional models, or other user-perceptible elements that are not actually present in the physical, real-world environment in which the virtual objects are presented as coexisting. In addition, virtual objects described in various examples of this disclosure may include graphics, images, animations or videos, e.g., presented as 3D virtual objects or 2D virtual objects. Virtual objects may also be referred to as virtual elements. Such elements may or may not be analogs of real-world objects. In some examples, in mixed reality, a camera may capture images of the real world and modify the images to present virtual objects in the context of the real world. In such examples, the modified images may be displayed on a screen, which may be head-mounted, handheld, or otherwise viewable by a user. This type of mixed reality is increasingly common on smartphones, such as where a user can point a smartphone's camera at a sign written in a foreign language and see in the smartphone's screen a translation in the user's own language of the sign superimposed on the sign along with the rest of the scene captured by the camera. In some examples, in mixed reality, see-through (e.g., transparent) holographic lenses, which may be referred to as waveguides, may permit the user to view real-world objects, i.e., actual objects in a real-world environment, such as real anatomy, through the holographic lenses and also concurrently view virtual objects.

In some examples, in mixed reality, the positions of some or all presented virtual objects are related to positions of physical objects in the real world. For example, a virtual object may be tethered to a table in the real world, such that the user can see the virtual object when the user looks in the direction of the table but does not see the virtual object when the table is not in the user's field of view. In some examples, in mixed reality, the positions of some or all presented virtual objects are unrelated to positions of physical objects in the real world. For instance, a virtual item may always appear in the top right of the user's field of vision, regardless of where the user is looking.

Augmented reality (AR) is similar to MR in the presentation of both real-world and virtual elements, but AR generally refers to presentations that are mostly real, with a few virtual additions to "augment" the real-world presentation. For purposes of this disclosure, MR is considered to include AR. For example, in AR, parts of the user's physical environment that are in shadow can be selectively brightened without brightening other areas of the user's physical environment. This example is also an instance of MR in that the selectively-brightened areas may be considered virtual objects superimposed on the parts of the user's physical environment that are in shadow.

Furthermore, in this disclosure, the term "virtual reality" (VR) refers to an immersive artificial environment that a user experiences through sensory stimuli (such as sights and sounds) provided by a computer. Thus, in virtual reality, the user may not see any physical objects as the physical objects exist in the real world. Video games set in imaginary worlds are a common example of VR. The term "VR" also encompasses scenarios where the user is presented with a fully artificial environment in which some virtual object's locations are based on the locations of corresponding physical objects as the corresponding physical objects relate to the user. Walk-through VR attractions are examples of this type of VR.

The term "extended reality" (XR) is a term that encompasses a spectrum of user experiences that includes virtual reality, mixed reality, augmented reality, and other user experiences that involve the presentation of at least some perceptible elements as existing in the user's environment that are not present in the user's real-world environment. Thus, the term "extended reality" may be considered a genus for MR and VR. XR visualizations may be presented in any of the techniques for presenting mixed reality discussed elsewhere in this disclosure or presented using techniques for presenting VR, such as VR goggles.

The following examples are illustrative of the techniques described herein.

Example 1: A medical system includes a medical device, configured to be positioned on a limb of a patient includes sound sensors; and vibration sensors; processing circuitry configured to: receive sensor data includes sound data, associated with blood flow, collected by the sound sensors; and vibration data, associated with blood flow, collected by the vibration sensors; and send the sensor data to a computing system.

Example 2: The medical system of example 1, wherein the processing circuitry is further configured to: receive from the computing system a diagnosis relating to an occurrence of at least one of stenosis or thrombosis; and output the diagnosis relating to the occurrence of the at least one of the stenosis or the thrombosis.

Example 3: The medical system of example 2, wherein the medical device includes a wearable sleeve including one or more subregions, wherein at least one of the sound sensors and at least one of the vibration sensors is located in each of the one or more subregions.

Example 4: The medical system of any of examples 2 and 3, wherein the sensors further includes temperature sensors and pulse sensors, and wherein the sensor data further includes one or more of pulse data or temperature data.

Example 5: The medical system of any of examples 1 through 4, wherein each of the sensors is located at a unique position with respect to the medical device and unique identification information, and wherein the processing circuitry is configured to send the sensor data collected by each sensor with the unique identification information of the sensor.

Example 6: The medical system of any of examples 1 through 5, wherein the medical system further includes an external device including the processing circuitry, wherein the processing circuitry is further configured to receive the sensor data collected by the medical device.

Example 7: The medical system of any of examples 1 through 6, wherein the processing circuitry is further configured to: process the sensor data to determine whether a likelihood of the occurrence of the at least one of the stenosis or the thrombosis exceeds a threshold risk of the occurrence of the at least one of the stenosis or the thrombosis; and responsive to determining that the sensor data indicates that the likelihood of the occurrence of the at least one of the stenosis or the thrombosis exceeds the threshold risk of the occurrence of the at least one of the stenosis or the thrombosis, send an indication to the computing system that the threshold risk of the occurrence of the at least one of the stenosis or the thrombosis is satisfied.

Example 8: The medical system of example 7, wherein the processing circuitry to determine the likelihood of the occurrence of the at least one of the stenosis or the thrombosis, the processing circuitry is configured to compare at least part of the sensor data to at least part of a corresponding template sensor data.

Example 9: The medical system of any of examples 7 and 8, wherein the processing circuitry is further configured to send the sensor data to a clinician for inspection based on the processing circuitry determining that the likelihood of the occurrence of the at least one of the stenosis or the thrombosis exceeds the threshold risk of the occurrence of the at least one of the stenosis or the thrombosis.

Example 10: The medical system of any of examples 1 through 9, wherein the medical system is configured to send the sensor data to a clinician in real-time.

Example 11: A diagnostic system includes a computing system configured to: receive sensor data from a processing circuitry, the sensor data includes sound data associated with blood flow; vibration data associated with blood flow; output devices includes a speaker configured to output a sound based on the sound data; and a haptic device configured to provide a haptic feedback based on the vibration data.

Example 12: The diagnostic system of example 11, wherein the computing system is further configured to send a diagnosis relating to an occurrence of at least one of stenosis or thrombosis.

Example 13: The diagnostic system of any of examples 11 and 12, wherein the haptic device includes a wearable glove including an actuator configured to provide the haptic feedback.

Example 14: The diagnostic system of any of examples 11 through 13, wherein the sensor data further includes temperature data on a part of a body of a patient, and wherein the diagnostic system further includes a display configured to display an indication of the temperature data.

Example 15: The diagnostic system of any of examples 11 through 14, wherein the computing system is further configured to receive the sensor data from the processing circuitry in real-time.

Example 16: The diagnostic system of any of examples 11 through 15, wherein the output devices includes a visualization device wearable by a user, wherein the visualization device is configured to receive user input corresponding to a selection of a virtual analog of a particular sensor of a medical device, and wherein the output devices are configured to, responsive to the visualization device receiving the user input, trigger output, by one or more of the output devices, a portion of the sensor data collected by the particular sensor.

Example 17: The diagnostic system of example 16, wherein the user input is a contact between the virtual analog of the particular sensor with a virtual analog of a part of the user's body.

Example 18: A method includes measuring, by sensors of a medical device, one or more physiological parameters of a patient, wherein the medical device is configured to be positioned on a limb of the patient, and wherein the sensors include sound sensors and vibration sensors; outputting, by the sensors, sensor data to processing circuitry, wherein the sensor data includes sound data associated with blood flood and vibration data associated with blood flow; and sending, by the processing circuitry, the sensor data to a computing system.

Example 19: The method of example 18, wherein the processing circuitry is further configured to: receive from a computing system a diagnosis relating to an occurrence of at least one of stenosis or thrombosis; and output the diagnosis relating to the occurrence of the at least one of the stenosis or the thrombosis.

Example 20: The method of any of examples 18 and 19, wherein the medical device includes a wearable sleeve including one or more subregions, wherein at least one of the sound sensors and at least one of the vibration sensors is located in each of the one or more subregions.

Various examples have been described. These and other examples are within the scope of the following claims.

What is claimed is:

1. A medical system comprising:
a medical device configured to be positioned on a limb of a patient at or proximate to a vascular access site, wherein the medical device includes sensors comprising:
one or more sound sensors;
one or more vibration sensors; and
one or more pulse sensors; and
processing circuitry configured to:
receive sensor data comprising:
sound data, associated with blood flow through the vascular access site, collected by the one or more sound sensors;
vibration data, associated with blood flow through the vascular access site, collected by the one or more vibration sensors; and
pulse data, associated with blood flow through the vascular access site, collected by the one or more pulse sensors; and
evaluate the sensor data to identify at least one blood flow anomaly; and
responsive to evaluating the sensor data, send at least one of an indication of the identified blood flow anomaly to a computing system,
wherein each of the sensors is located at a unique position with respect to the medical device and includes unique identification information, and
wherein the processing circuitry is configured to send the sensor data collected by each sensor with the unique identification information of the sensor.

2. The medical system of claim 1, wherein the processing circuitry is further configured to:
receive from the computing system a diagnosis relating to an occurrence of at least one of stenosis or thrombosis; and
output the diagnosis relating to the occurrence of the at least one of the stenosis or the thrombosis.

3. The medical system of claim 1, wherein the medical device comprises a wearable sleeve comprising one or more subregions, wherein at least one of the one or more sound sensors and at least one of the one or more vibration sensors is located in each of the one or more subregions.

4. The medical system of claim 1,
wherein the sensors further comprises one or more temperature sensors, and
wherein the sensor data further comprises temperature data collected by the one or more temperature sensors.

5. The medical system of claim 1, wherein the processing circuitry is further configured to:
process the sensor data to determine whether a likelihood of an occurrence of at least one of stenosis or thrombosis exceeds a threshold risk of the occurrence of the at least one of the stenosis or the thrombosis; and
responsive to determining that the sensor data indicates that the likelihood of the occurrence of the at least one of the stenosis or the thrombosis exceeds the threshold risk of the occurrence of the at least one of the stenosis or the thrombosis, send an indication to the computing system that the threshold risk of the occurrence of the at least one of the stenosis or the thrombosis is satisfied.

6. The medical system of claim 1, wherein the medical system is configured to send the sensor data to a clinician in real-time.

7. A diagnostic system comprising:
a computing system configured to:
receive sensor data from a processing circuitry, the sensor data comprising:
sound data associated with blood flow through a vascular access site;
vibration data associated with blood flow through the vascular access site; and
pulse data associated with blood flow through the vascular access site; and
evaluate the sensor data to identify at least one blood flow anomaly; and
output devices comprising:
a speaker configured to output a sound based on the sound data; and
a haptic device configured to provide a haptic feedback based on the vibration data; and
a visualization device wearable by a user,
wherein the visualization device is configured to receive user input corresponding to a selection of a virtual analog of a particular sensor of a medical device, and
wherein the output devices are configured to, responsive to the visualization device receiving the user input, trigger output of a portion of the sensor data collected by the particular sensor.

8. The diagnostic system of claim 7, wherein the computing system is further configured to send a diagnosis relating to an occurrence of at least one of stenosis or thrombosis.

9. The diagnostic system of claim 7, wherein the haptic device comprises a wearable glove comprising an actuator configured to provide the haptic feedback.

10. The diagnostic system of claim 7, wherein the sensor data further comprises temperature data on a part of a body of a patient, and wherein the diagnostic system further comprises a display configured to display an indication of the temperature data.

11. The diagnostic system of claim 7, wherein the computing system is further configured to receive the sensor data from the processing circuitry in real-time.

12. The diagnostic system of claim 7, wherein the user input is a contact between the virtual analog of the particular sensor with a virtual analog of a part of a body of the user.

13. A method comprising:
measuring, by sensors of a medical device, one or more physiological parameters of a patient, wherein the medical device is positioned on a limb of the patient at or proximate to a vascular access site, and wherein the sensors comprise one or more sound sensors, one or more vibration sensors, and one or more pulse sensors;
outputting, by the sensors, sensor data to processing circuitry, wherein the sensor data comprises:
sound data associated with blood flow through the vascular access site;
vibration data associated with blood flow through the vascular access site; and
pulse data associated with blood flow through the vascular access site; and
determining, by the processing circuitry, whether the sensor data indicates that a likelihood of an occurrence of at least one of stenosis or thrombosis exceeds a threshold risk of the occurrence of the at least one of the stenosis or the thrombosis; and
responsive to determining that the sensor data indicates that the likelihood of the occurrence of the at least one of the stenosis or the thrombosis exceeds the threshold risk of the occurrence of the at least one of the stenosis or the thrombosis, sending, by the processing circuitry, an indication that the threshold risk of the occurrence of the at least one of the stenosis or the thrombosis is satisfied to a computing system.

14. The method of claim 13, wherein the medical device comprises a wearable sleeve comprising one or more subregions, wherein at least one of the sound sensors and at least one of the vibration sensors is located in each of the one or more subregions.

15. A medical system comprising:
a medical device configured to be positioned on a limb of a patient at or proximate to a vascular access site, wherein the medical device includes sensors comprising:
one or more sound sensors;
one or more vibration sensors; and
one or more pulse sensors; and
processing circuitry configured to:
receive sensor data comprising:
sound data, associated with blood flow through the vascular access site, collected by the one or more sound sensors;
vibration data, associated with blood flow through the vascular access site, collected by the one or more vibration sensors; and
pulse data, associated with blood flow through the vascular access site, collected by the one or more pulse sensors; and
process the sensor data to determine whether a likelihood of an occurrence of at least one of stenosis or thrombosis exceeds a threshold risk of the occurrence of the at least one of the stenosis or the thrombosis; and
responsive to determining that the sensor data indicates that the likelihood of the occurrence of the at least one of the stenosis or the thrombosis exceeds the threshold risk of the occurrence of the at least one of the stenosis or the thrombosis, send an indication to a computing system that the threshold risk of the occurrence of the at least one of the stenosis or the thrombosis is satisfied.

16. The medical system of claim 15, wherein to determine whether the likelihood of the occurrence of the at least one of the stenosis or the thrombosis exceeds the threshold risk, the processing circuitry is configured to compare at least part of the sensor data to at least part of a corresponding template sensor data.

17. The medical system of claim 15, wherein the processing circuitry is further configured to send the sensor data to a clinician for inspection based on the processing circuitry determining that the likelihood of the occurrence of the at least one of the stenosis or the thrombosis exceeds the threshold risk of the occurrence of the at least one of the stenosis or the thrombosis.

* * * * *